(12) United States Patent
Ariyama et al.

(10) Patent No.: US 11,298,031 B2
(45) Date of Patent: Apr. 12, 2022

(54) SPHYGMOMANOMETER, BLOOD PRESSURE MEASUREMENT METHOD, AND BLOOD PRESSURE MEASUREMENT PROGRAM

(71) Applicant: NEC Corporation, Tokyo (JP)

(72) Inventors: Tetsuri Ariyama, Tokyo (JP); Masahiro Kubo, Tokyo (JP); Katsumi Abe, Tokyo (JP); Ersin Altintas, Tokyo (JP); Yuji Ohno, Tokyo (JP); Takeshi Akagawa, Tokyo (JP)

(73) Assignee: NEC CORPORATION, Tokyo (JP)

( * ) Notice: Subject to any disclaimer, the term of this patent is extended or adjusted under 35 U.S.C. 154(b) by 328 days.

(21) Appl. No.: 16/086,078

(22) PCT Filed: Mar. 17, 2017

(86) PCT No.: PCT/JP2017/010998
§ 371 (c)(1),
(2) Date: Sep. 18, 2018

(87) PCT Pub. No.: WO2017/169924
PCT Pub. Date: Oct. 5, 2017

(65) Prior Publication Data
US 2020/0288984 A1  Sep. 17, 2020

(30) Foreign Application Priority Data
Mar. 29, 2016  (JP) .............................. JP2016-065726

(51) Int. Cl.
*A61B 5/022* (2006.01)
*A61B 5/021* (2006.01)
*A61B 5/00* (2006.01)

(52) U.S. Cl.
CPC .......... *A61B 5/022* (2013.01); *A61B 5/02141* (2013.01); *A61B 5/742* (2013.01); *A61B 2562/0247* (2013.01)

(58) Field of Classification Search
CPC ..... A61B 5/022; A61B 5/02141; A61B 5/742; A61B 2562/0247
See application file for complete search history.

(56) References Cited

U.S. PATENT DOCUMENTS

| 4,751,930 A | 6/1988 | Terada et al. |
| 5,564,426 A * | 10/1996 | Iwai ........................ A61B 5/022 600/493 |

(Continued)

FOREIGN PATENT DOCUMENTS

| JP | 62-14831 A | 1/1987 |
| JP | 3-121045 A | 5/1991 |

(Continued)

OTHER PUBLICATIONS

International Search Report dated Jun. 13, 2017 from the International Searching Authority in counterpart International Application No. PCT/JP2017/010998.

(Continued)

*Primary Examiner* — Devin B Henson
*Assistant Examiner* — Joseph A Tombers (57) ABSTRACT

The purpose of the present invention is to provide a sphygmomanometer that has a high level of measurement accuracy and places a low burden upon a subject whose systolic pressure is being measured. To this end, the sphygmomanometer according to the present invention is characterized by comprising: a cuff pressure and pulse wave detecting unit that detects cuff pressure and pulse waves; and a blood pressure calculating unit that divides pulse waves detected by the cuff pressure and pulse wave detecting unit into a plurality of sections within a specific period, and calculates an estimated value for systolic pressure on the basis of fluctuations in the symmetry of the pulse wave waveform in the plurality of sections, said fluctuations occurring along with variations in the cuff pressure detected by the cuff pressure and pulse wave detecting unit.

7 Claims, 9 Drawing Sheets

(56) References Cited

U.S. PATENT DOCUMENTS

| | | | |
|---|---|---|---|
| 5,606,977 A | 3/1997 | Ramsey, III et al. | |
| 2005/0119578 A1 | 6/2005 | Kubo | |
| 2011/0251500 A1* | 10/2011 | Sawanoi | ................ G01G 19/50 600/494 |
| 2015/0230718 A1* | 8/2015 | Whitaker | ........... A61B 5/02116 600/492 |

FOREIGN PATENT DOCUMENTS

| | | |
|---|---|---|
| JP | 6-319708 A | 11/1994 |
| JP | 8-280640 A | 10/1996 |
| JP | 2001-187033 A | 7/2001 |
| JP | 2003-284696 A | 10/2003 |
| WO | 94/04074 A1 | 3/1994 |
| WO | 2009/142266 A1 | 11/2009 |
| WO | 2010/071052 A1 | 6/2010 |

OTHER PUBLICATIONS

Japanese Office Action for JP Application No. 2018-509062 dated Feb. 8, 2022 with English Translation.

* cited by examiner

SPHYGMOMANOMETER, BLOOD PRESSURE MEASUREMENT METHOD, AND BLOOD PRESSURE MEASUREMENT PROGRAM

This application is a National Stage Entry of PCT/JP2017/010998 filed on Mar. 17, 2017, which claims priority from Japanese Patent Application 2016-065726 filed on Mar. 29, 2016, the contents of all of which are incorporated herein by reference, in their entirety.

TECHNICAL FIELD

The present invention relates to a sphygmomanometer, a blood pressure measurement method, and a blood pressure measurement program.

BACKGROUND ART

As a method for measuring a blood pressure, in general, there are an auscultation method and an oscillometric method.

In the auscultation method, a cuff (arm belt) is wrapped around an arm of a person to be measured; the cuff is pressurized first and then depressurized; and a sound of a blood vessel (Korotkoff sound=K-sound) generated when blood starts to flow intermittently in pace with pulsation of a heart is listened to with a stethoscope. A cuff pressure at the start of the K-sound generation is estimated to be a systolic blood pressure (or a maximal blood pressure) while a cuff pressure when the K-sound is lost is treated as a diastolic blood pressure (or a minimal pressure). The auscultation method is a standard method for blood pressure measurement, and it is often performed by a human such as a doctor or a nurse. Values measured by means of the auscultation method have become reference values for blood pressure.

In the oscillometric method, a blood pressure is measured, based on a pulse wave instead of the K-sound. A pulse wave is an oscillation generated in pace with a heartbeat by a blood vessel compressed by a cuff. Utilizing fluctuation in pressure caused by pulsation of an artery that propagates to the cuff, the blood pressure is measured. At a step of pressurizing and then depressurizing the cuff, the blood pressure is determined by sensing fluctuation of the cuff pressure (pressure pulse wave), which reflects oscillations of a blood vessel wall in synchronization with pulsation of the heart. In general, the cuff pressure when the pressure pulse wave sharply increases is estimated to be the systolic blood pressure while the cuff pressure when the pressure pulse wave sharply decreases is estimated to be the diastolic blood pressure. The oscillometric method is suitable for automatic blood pressure measurement, and it is widely adopted in sphygmomanometers for home use.

However, in both the auscultation method and the oscillometric method, the cuff is pressurized to the systolic blood pressure or above. Since the systolic blood pressure of a person to be measured is obviously not known before measurement, applying a pressure higher than the systolic blood pressure is necessary, which imposes great burden on elderly persons, patients (particularly, hypertensive patients), injured persons and the like and gives them uncomfortable feeling. Therefore, it is desirable to reduce magnitude of the applied pressure as much as possible. It is also desirable that the measurement time is as short as possible.

PTL 1 (Japanese Unexamined Patent Application Publication No. 2003-284696) discloses a high-precision electronic sphygmomanometer that can measure a systolic blood pressure without pressurization beyond the systolic blood pressure. This sphygmomanometer first determines a mean blood pressure and a diastolic blood pressure by means of the oscillometric method or other method. An arterial blood pressure waveform representing the blood pressure itself has a similarity to a pulse waveform generated upon compression by a cuff. A pulse wave upon compression by the cuff (ST1) is detected, based on the similarity (ST2), and an estimated mean blood pressure is obtained from a maximum amplitude of the pulse wave (ST3, ST4). The estimated mean blood pressure and a minimum value of the pulse waveform are respectively regarded as the mean blood pressure and the diastolic blood pressure (ST6, ST7), and the systolic blood pressure is obtained from a maximum value of the pulse waveform by calculation (ST9).

In PTL 1, it is assumed that the mean blood pressure is equal to the cuff pressure when a pressure pulse wave reaches the maximum amplitude value and the systolic blood pressure SBP is estimated using the following equation described in PTL 1. EMAP represents the mean blood pressure, DBP represents the diastolic blood pressure, AAV represents the mean value of the waveform, and a represents a correction factor.

$$SBP = Am^*\alpha(EMAP-DBP)/AAV+DBP$$

Furthermore, PTL 2 (Japanese Unexamined Patent Application Publication No. 1996-280640) discloses a technique for distinguishing between an amplitude measured during diastole and an amplitude measured during systole. Ratios (Au/Aut, Ad/Adt) of areas Au and Ad defined by the curve of the pulse wave illustrated in FIG. 4 of PTL 2 to areas Aut and Adt of triangles B-A-B' and B-B'-A' illustrated in FIG. 4 of PTL 2 are calculated. It is determined that the area ratio being equal to or greater than 1 indicates systole and that the area ratio being equal to or smaller than 1 indicates diastole (paragraphs [0039] to [0046] and [0013] to [0014]).

CITATION LIST

Patent Literature

[PTL 1] Japanese Unexamined Patent Application Publication No. 2003-284696
[PTL 2] Japanese Unexamined Patent Application Publication No. 1996-280640

SUMMARY OF THE INVENTION

Technical Problem

PTL 1 aims at realizing high-precision systolic blood pressure measurement without applying a pressure higher than a systolic blood pressure, and to achieve this object, the systolic blood pressure is obtained from a mean blood pressure and a minimum value of a pulse waveform by means of the aforementioned equation.

However, the mean blood pressure is not always equal to the cuff pressure when the pressure pulse wave reaches the maximum amplitude value. In other words, the systolic blood pressure obtained using the equation proposed in PTL 1 is inaccurate, and a difference from a blood pressure obtained by means of the auscultation method, which is a reference value, is large.

Furthermore, PTL 2 is a technique for distinguishing between an amplitude measured during diastole and an amplitude measured during systole, and it is not for accurately measuring a systolic blood pressure.

An object of the present invention is to provide a sphygmomanometer, a blood pressure measurement method, and a blood pressure measurement program that solve the aforementioned problems and that have high measurement accuracy and yet impose less burden on a person to be measured when measuring the systolic blood pressure.

Solution to the Problem

The present invention is a sphygmomanometer characterized in that the sphygmomanometer includes a cuff pressure and pulse wave detecting unit configured to detect a cuff pressure and a pulse wave and a blood pressure calculating unit configured to divide the pulse wave detected by the cuff pressure and pulse wave detecting unit in a particular period into a plurality of sections and calculate an estimated value of a systolic blood pressure from fluctuation in symmetry of pulse waveforms of the plurality of sections caused by variation of the cuff pressure detected by the cuff pressure and pulse wave detecting unit.

The present invention is also a blood pressure measurement method characterized in that a cuff pressure and a pulse wave are detected, the detected pulse wave is divided in a particular period into a plurality of sections, and an estimated value of a systolic blood pressure is calculated from fluctuation in symmetry of pulse waveforms of the plurality of sections caused by variation of the detected cuff pressure.

The present invention is also a blood pressure measurement program characterized in that the program causes a computer to execute a cuff pressure and pulse wave detecting process for detecting a cuff pressure and a pulse wave as well as a process for dividing the pulse wave detected by the cuff pressure and pulse wave detecting unit in a particular period into a plurality of sections and calculating an estimated value of a systolic blood pressure from fluctuation in symmetry of pulse waveforms of the plurality of sections caused by variation of the cuff pressure detected by the cuff pressure and pulse wave detecting unit.

Advantageous Effects of the Invention

According to the present invention, it is possible to provide a sphygmomanometer, a blood pressure measurement method, and a blood pressure measurement program that have high measurement accuracy and yet impose less burden on a person to be measured when measuring the systolic blood pressure.

BRIEF DESCRIPTION OF DRAWINGS

FIG. 4($a$) illustrates a pulse waveform of a subject while FIG. 4($b$) is a graph of cuff pressures and feature values generated by means of calculated area ratios.

EXAMPLE EMBODIMENT

First Example Embodiment

[Description of the Configuration]

By means of FIG. 1 to FIG. 4, a first example embodiment according to the present invention will be described.

Figure 1:
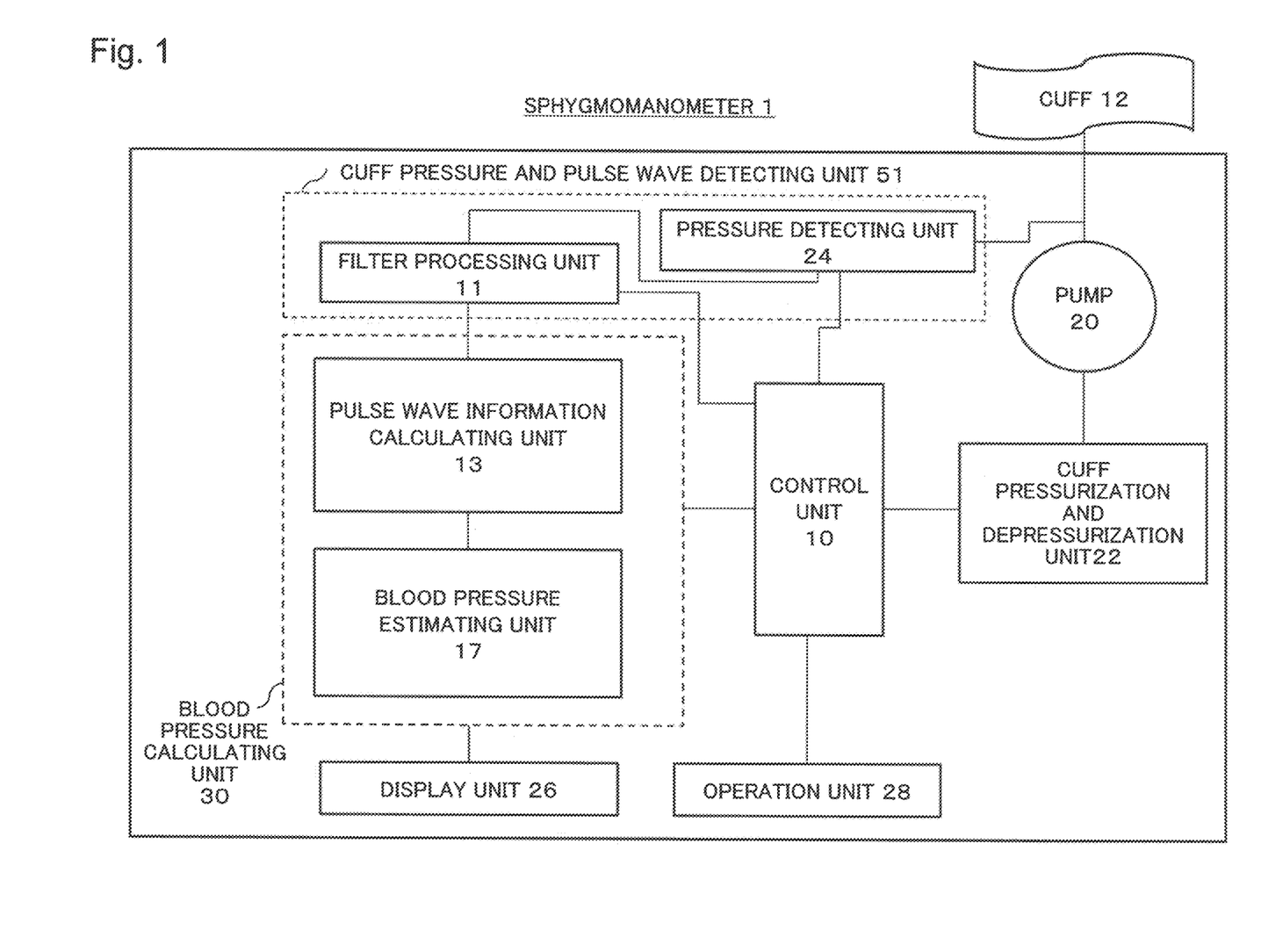
FIG. 1 is a block diagram illustrating a configuration of a sphygmomanometer of a first example embodiment according to the present invention.

FIG. 1 is a block diagram illustrating a configuration of a sphygmomanometer 1 of the present example embodiment.

Figure 10:
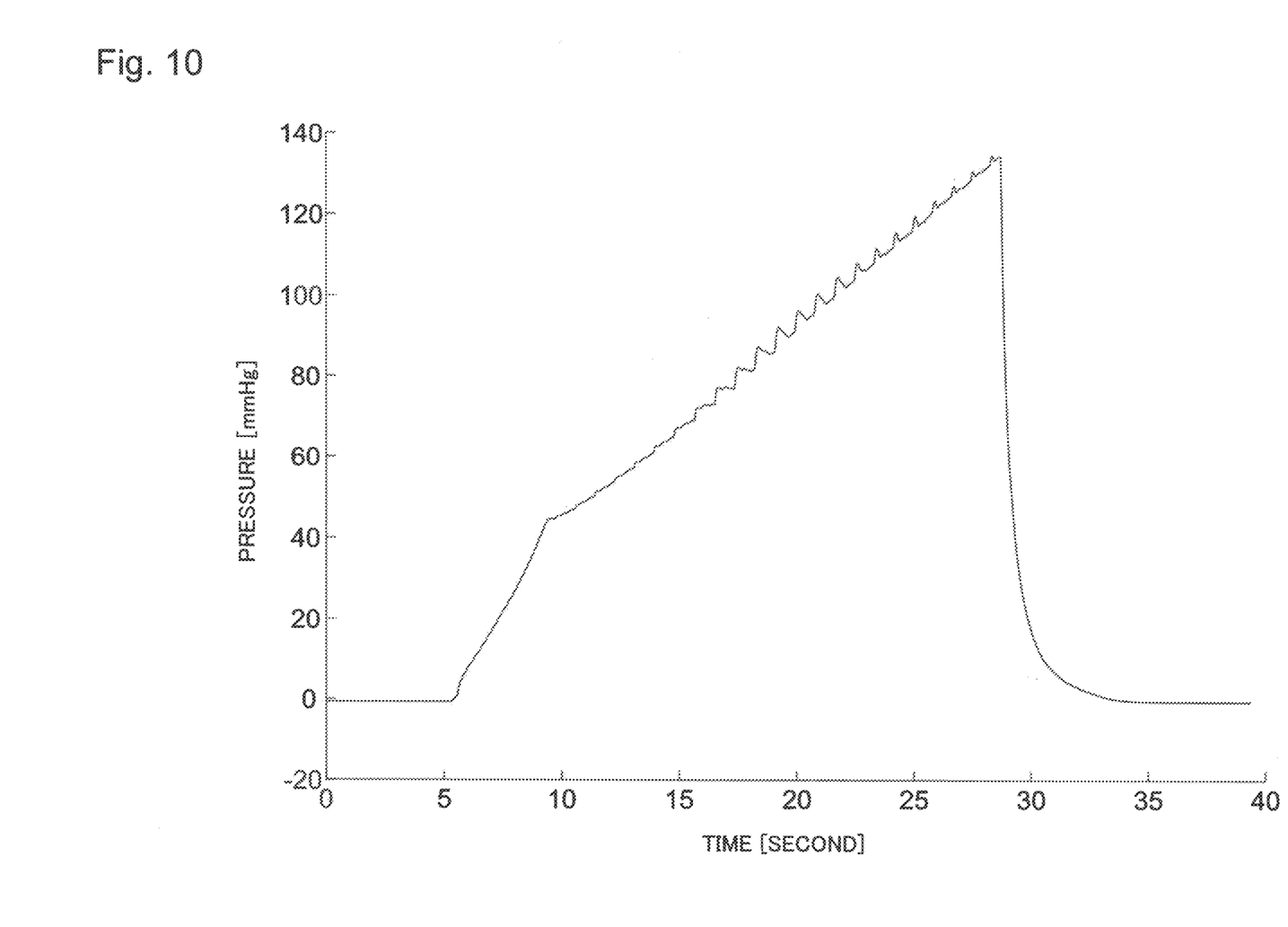
FIG. 10 is a chart schematically illustrating a temporal variation of the cuff pressure and the pulse wave.

A control unit 10 controls the whole sphygmomanometer. A pressure detecting unit 24 acquires a raw waveform propagating from a cuff 12 by means of a pressure sensor. The raw waveform detects a pressure in which a pressure applied with pneumatic pressure (hereinafter, referred to as a cuff pressure) and a pulse wave are combined. A filter processing unit 11 divides the raw waveform into the cuff pressure and the pulse wave. FIG. 10 is a chart illustrating an example of the raw waveform in which the cuff pressure and the pulse wave are combined.

A pulse wave information calculating unit 13 detects extreme values (peak values) of the signal of the pulse wave obtained by the filter processing unit 11. The pulse wave information calculating unit 13 further calculates, with dividing the pulse wave at a point of time at which the detected maximal value for each pulse appears, an area S1 of the pulse wave before the maximal value and an area S2 of the pulse wave after the maximal value, and calculates an area ratio S1/S2.

A blood pressure estimating unit 17 generates a relational expression f(X) from the area ratio S1/S2 calculated by the pulse wave information calculating unit 13 and the cuff pressure.

The blood pressure estimating unit 17 also treats the cuff pressure corresponding to f(1) obtained by means of the relational expression f(X) that it generated as an estimated value of the systolic blood pressure.

The pulse wave information calculating unit 13 and the blood pressure estimating unit 17 are collectively referred to as a blood pressure calculating unit 30. The pressure detecting unit 24 and the filter processing unit 11 are collectively referred to as a cuff pressure and pulse wave detecting unit 51.

The sphygmomanometer 1 also includes a pump 20 for pressurizing the cuff with pneumatic pressure and generating a cuff pressure; a cuff pressurization and depressurization unit 22 for controlling pressurization and depressurization of the pump 20; a pressure detecting unit 24; an operation unit 28 such as a button; and a display unit 26 for displaying a blood pressure and the like.

[Description of the Operation]

A person to be measured wraps a cuff 12 around an upper arm where a pulse wave may be detected from an artery, and presses a button or the like of the operation unit 28. The control unit 10 sends an instruction of pressurization to the cuff pressurization and depressurization unit 22 in accordance with a measurement sequence stored therein, and the cuff pressurization and depressurization unit 22 instructs the pump 20 on a pneumatic pressure to be pushed out accordingly. The cuff pressure measured by a pressure sensor of the cuff 12 is detected by the pressure detecting unit 24. As air is delivered to the cuff, the cuff pressure rises.

Figure 2:
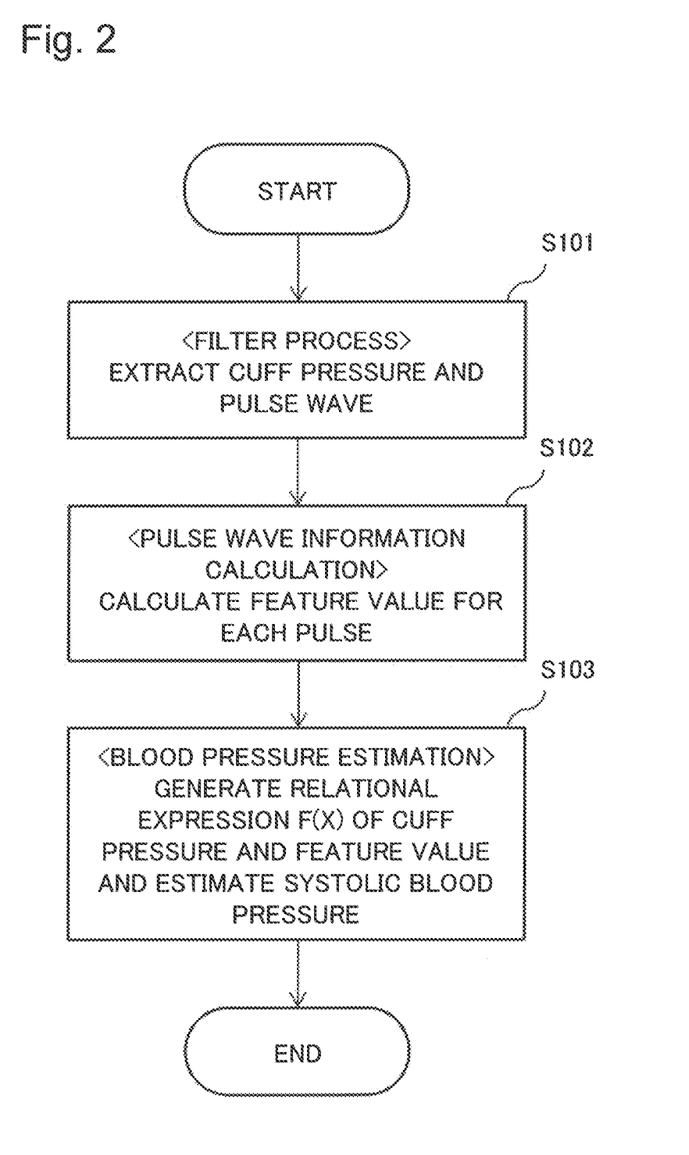
FIG. 2 is a diagram for explaining an operation of the sphygmomanometer of the first example embodiment according to the present invention.
Figure 3:
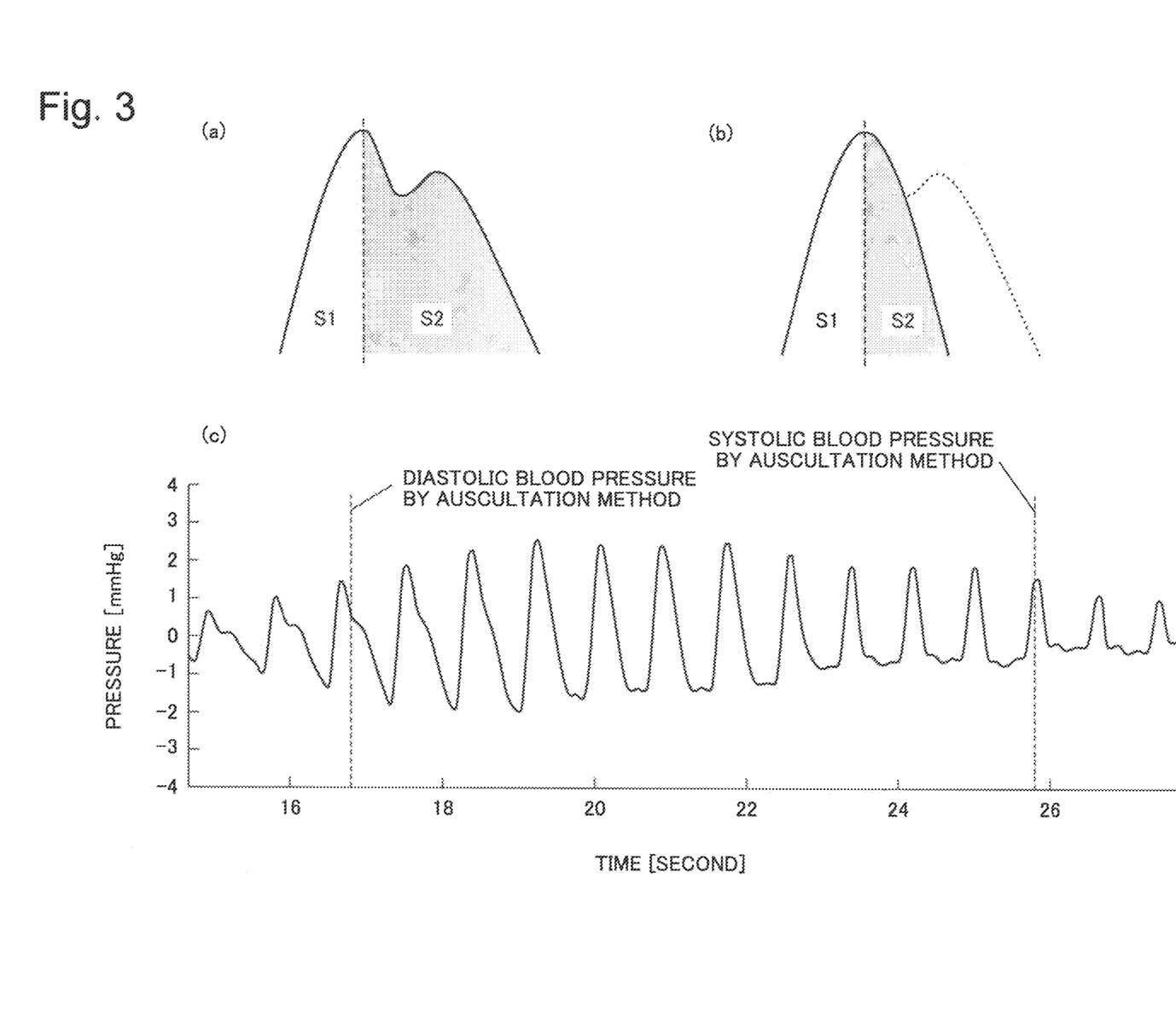
FIG. 3 is a diagram for explaining a measurement technique of the sphygmomanometer of the first example embodiment according to the present invention.

FIG. 2 is a diagram for explaining an operation of the sphygmomanometer of the present example embodiment. The detected value includes both the cuff pressure and the amplitude of the pulse wave. Therefore, the pulse wave is extracted by means of an HPF (High Pass Filter) of the filter processing unit 11 (S101). The cuff pressure is extracted by means of an LPF (Low Pass Filter). The extracted cuff pressure is used at S103 to be described later.

Subsequently, pulse wave information is calculated. (S102).

FIGS. 3(a), 3(b), and 3(c) are diagrams for explaining a measurement technique of the sphygmomanometer of the present example embodiment. FIG. 3(c) illustrates a waveform after only the pulse wave is extracted, where the horizontal axis represents the measurement time (second) and the vertical axis represents the pressure waveform (mmHg) of the pulse wave. Vertical dashed lines in FIG. 3(c) represents the systolic blood pressure and the diastolic blood pressure by means of the existing auscultation method.

FIGS. 3(a) and 3(b) are schematic diagrams illustrating an enlarged pulse waveform for a pulse. In the pulse wave, an ejected wave generated due to contraction of a heart for delivering blood to an entire body and a reflected wave generated due to reflection of the ejected wave at a peripheral artery, an arterial bifurcation, or the like during delivery of the ejected wave to the entire body are overlapped. FIG. 3(a) illustrates a pulse waveform when the cuff pressure is around the DBP (diastolic blood pressure). In contrast, FIG. 3(b) illustrates a pulse waveform when the cuff pressure is around the SBP (systolic blood pressure). In FIG. 3(a), existence of the reflected wave is visible. On the other hand, in FIG. 3(b), the reflected wave is not visible since the reflected wave tends to gradually attenuate as the cuff pressure rises.

Now, an area of the waveform between a local minimum value and a maximal value of the pulse waveform for a pulse (S1, hereinafter, referred to as an area of the pulse wave before the maximal value) and an area of the waveform between the maximal value and the next local minimum value of the pulse waveform for a pulse (S2, hereinafter, referred to as an area of the pulse wave after the maximal value) are compared (S102). Note that the "next local minimum value" means a local minimum value occurring at or near the end of the pulse wave for a pulse. In FIG. 3(a), S1/S2<1 holds while in FIG. 3(b), the area ratio S1/S2≈1. Looking at the pulse waveform in FIG. 3(c), as the cuff is pressurized, the reflected wave overlapping the ejected wave gradually attenuates, and the pulse waveform becomes line-symmetric about the point of time at which a maximal value appears; in other words, S1/S2≈1. Inventors of the present invention have found that the pressure of the pulse wave at a timing where S1/S2≈1 holds coincides with the systolic blood pressure. This will be described below.

FIG. 4(a) illustrates a pulse waveform (mmHg) of a certain subject while FIG. 4(b) is a graph of the cuff pressure and a feature value (in the present example embodiment, an area ratio of S1 to S2) generated by means of calculated area ratios. The area ratio S1/S2 for each pulse of the pulse wave detected after the cuff is pressurized is calculated. The area ratio is calculated by measuring a maximal value for each pulse of the obtained pulse wave and integrating from a local minimum value and the maximal value and from the maximal value and the next local minimum value. The area ratio may be obtained by means of other methods. The pulse wave information calculating unit 13 detects the maximal value and the local minimum value, and calculates areas and the area ratio.

FIG. 4(b) is a graph obtained by making a graph of the cuff pressure and a feature value with plotting the feature value on the vertical axis and the cuff pressure (mmHg) on the horizontal axis and generating a relational expression f(X) by means of the least-squares method. A dashed line located at the cuff pressure=121 mmHg indicates the systolic blood pressure by means of the auscultation method.

Figure 4:
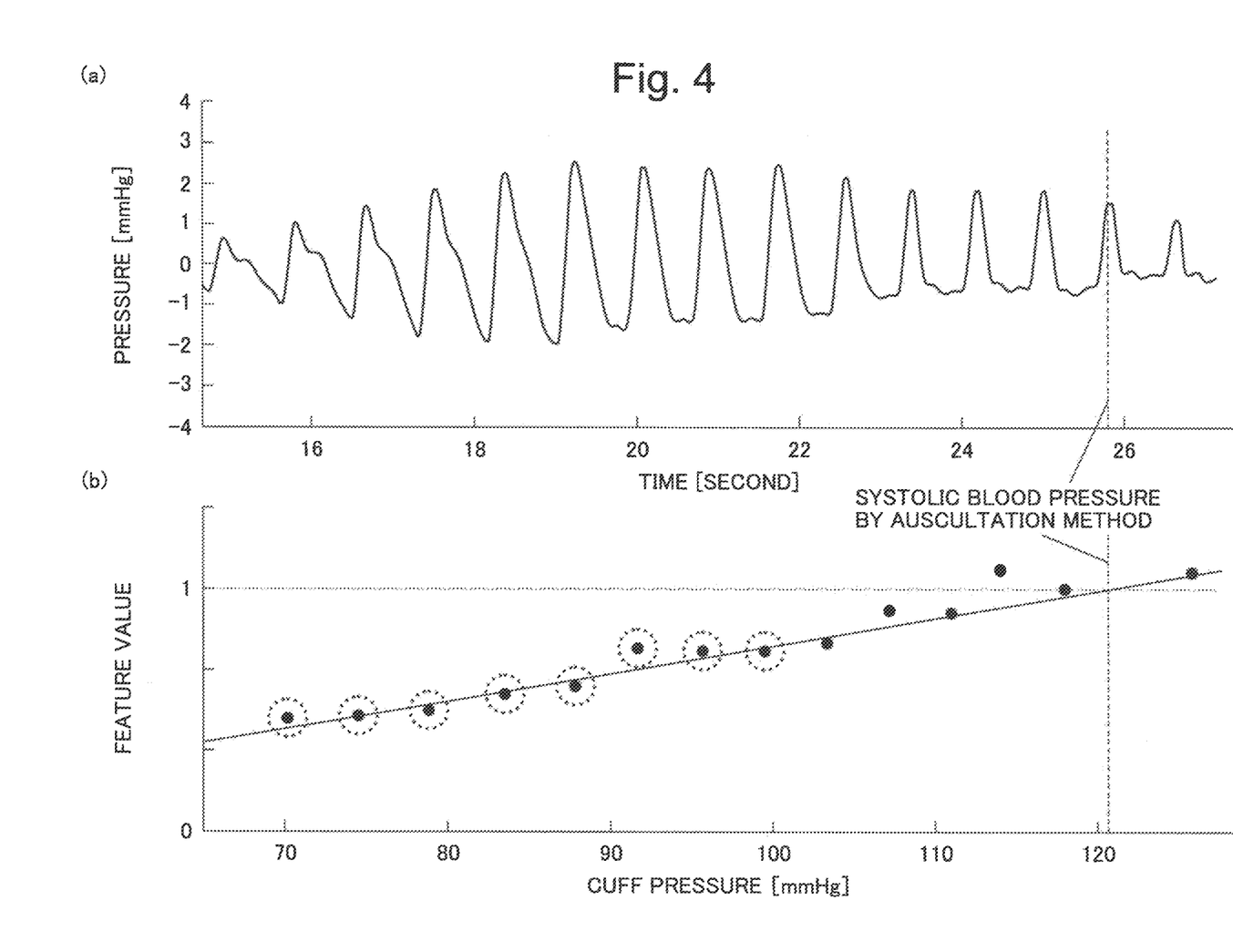

It is understood that at the time of f(1) in the relational expression, i.e., when the area ratio S1/S2=1, the cuff pressure of 121 mmHg well coincides with the systolic blood pressure measured by means of the auscultation method. Since the case of FIG. 4 is a trial, a pressure higher than the systolic blood pressure is applied. However, in practice, pressurization of the cuff is stopped before reaching the systolic blood pressure, and depressurization is immediately performed. By generating a relational expression from the plotted values obtained before pressurization is stopped and calculating f(1) by extrapolation using the relational expression, the systolic blood pressure may be accurately estimated before the cuff pressure reaches the systolic blood pressure (S103 in FIG. 2). The systolic blood pressure is estimated by the blood pressure estimating unit 17.

For measurement of the diastolic blood pressure, an existing method such as the oscillometric method may be used. In other words, during a step of pressurizing the cuff, the diastolic pressure, i.e., the diastolic blood pressure is measured; subsequently, the systolic blood pressure may be measured by means of the method of the present example embodiment.

[Description of the Effect]

In the present example embodiment, pressurization is stopped before the cuff pressure reaches the systolic blood pressure, and the systolic blood pressure is estimated by calculating a feature value from the pulse wave obtained before this point. Therefore, applying a pressure lower than that for existing methods such as the oscillometric method will suffice. For example, in FIG. 4(b), for a subject the systolic blood pressure of which is 121 mmHg, pressure is applied up to 130 mmHg (located on the extreme right in FIG. 4(b)) in the oscillometric method. In contrast, it is understood that, in the present example embodiment, the systolic blood pressure may be estimated from the pulse wave obtained during pressurization up to about 100 mHg (the rightmost one of the plotted values enclosed by a dotted line). In addition, it is found from FIG. 4(a) that it takes about 28 seconds with the oscillometric method while measurement may be complete in about 21 seconds with the present example embodiment. In other words, the present example embodiment may reduce pressure to be applied and shorten the measurement time, thus, the present example embodiment may reduce burden on a person to be measured.

In general, there is a large variation in blood pressure; therefore, blood pressure may be measured for 24 hours. For example, if measurement is made four times in an hour, an attachment site is compressed by the cuff each time measurement is made, i.e., about 100 times a day, which imposes very heavy burden on the subject. In contrast, the sphygmomanometer of the present example embodiment enables high-precision measurement, reduces compressive pressure applied to the attachment site by the cuff, and shortens a pressurization time; thus, the sphygmomanometer of the present example embodiment may significantly reduce burden imposed on the subject.

Note that, in the present example embodiment, by using an area ratio as a feature value and calculating a variation of the feature value, a cuff pressure when the feature value becomes a certain predetermined value is estimated to be the systolic blood pressure. The variation of the feature value may be interpreted as fluctuation in symmetry of pulse waveforms in a plurality of sections caused by variation of the cuff pressure.

Furthermore, in the present example embodiment, the area ratio is calculated with dividing the pulse wave at a point of time at which a maximal value of a pulse wave appears. However, with dividing the pulse wave at a point of time shifted from the point of time for the maximal value, the feature value for the pulse wave before and after this point of time, which may be an area ratio or the like, may be calculated, and a cuff pressure when the feature value ratio becomes a predetermined value other than 1 may be estimated to be the systolic blood pressure. In what way the area ratio may be defined, variation of a pulse wave, i.e., that the reflected wave overlapping the ejected wave gradually attenuates and only the ejected wave becomes visible as the cuff is pressurized remains unchanged (see FIG. 3). Therefore, even when the area ratio defined with dividing the pulse wave at a point of time shifted from the point of time for the maximal value is used, the systolic blood pressure may be estimated similarly to the case where the area ratio defined with dividing the pulse wave at the point of time for the maximal value is used. When dividing the pulse wave at a point of time temporally earlier than the point of time for the maximal value, S1/S2, which is estimated to be the systolic blood pressure, becomes less than 1. On the other hand, when dividing the pulse wave at a point of time temporally later than the point of time for the maximal value, S1/S2, which is estimated to be the systolic blood pressure, becomes greater than 1.

In the present example embodiment, areas between the two local minimum values and the maximal value have been also calculated. However, instead of using the local minimum values, by calculating a feature value such as an area ratio calculated from areas defined between points having values of m % of the wave height and the maximal value, a cuff pressure when the feature value ratio becomes a predetermined value other than 1 may be estimated to be the systolic blood pressure. Since the value of m is different depending on groups of subjects (for example, groups of subjects having a different arm circumference, race, or the like), the value of m may be determined by means of a statistical approach in such a way as to minimize an error using a number of subject data from the target group of subjects.

Alternatively, an area of a pulse waveform between the point of time for the maximal value and the point of time at which a pulse pressure of the pulse wave becomes 0 mmHg may be used.

Note that, although the area ratio is S1/S2 in the present example embodiment, it may be S2/S1.

In the present example embodiment, measurement is made until the N-th (N=0, 1, ...) pulse wave appears after a maximum amplitude of a pulse wave appears, and pressurization of the cuff is stopped at that point of time. However, not until the N-th (N=0, 1, ...) pulse wave after a maximum amplitude of a pulse wave appears, pressurization may be stopped at a point of time at which a feature value becomes a certain value (for example, S1/S2=0.7). Alternatively, before values of the cuff pressures and the feature values to be plotted in FIG. 4(b) are measured, it may be predetermined to calculate, for example, only five values having the smallest cuff pressures, and the systolic blood pressure may be estimated with stopping pressurization after the five values are calculated. The number of plotted values is not limited to five, and may be any number that enables accurate generation of a relational expression. Although, in the case of FIG. 4(b), the number of plotted values is eight, five values will enable measurement to be made in a short period of time. As long as accuracy is within the predetermined acceptable range, this approach is effective for applications where faster measurement is desired. Alternatively, pressurization may be stopped at a point of time at which the diastolic blood pressure is determined during pressurization. Pressurization may be stopped at a point of time at which T seconds have passed since the start of measurement or P mmHg is applied. It is just required that pressurization is stopped before the cuff pressure reaches the systolic blood pressure. When a high-precision measurement is desired, measurement may be continued until the area ratio=1. A switch that enables selection of a case where a high-precision measurement is desired and a case where high precision is not required may be included in the sphygmomanometer, and selection of a high-precision mode and a normal mode may be made.

Although the cuff is wrapped around an upper arm containing a brachial artery of a person to be measured in the present example embodiment, the cuff may be wrapped for measurement around a different site that contains, not limited to a brachial artery, a carotid artery, a superficial temporal artery, a facial artery, a radial artery, a femoral artery, a popliteal artery, a posterior tibial artery, a dorsalis pedis artery, or the like. As long as the site allows detection of a pulse wave from an artery, measurement may be made anywhere.

Furthermore, although a pulse waveform is divided into two sections in the present example embodiment, the number of sections is not limited to two, and the waveform may be divided into a plurality of sections. For example, when a pulse wave for a pulse may be divided into three sections in temporal order, respective areas may be S'1, S'2, and S'3, and (S'1+S'2)/S'3 may be defined as a feature value. As described above, as the cuff is pressurized, the reflected wave overlapping the ejected wave gradually attenuates. In response to this change, S'1, S'2, and S'3 vary on a certain trend similarly to S1 and S2 in the case of division into two sections. Therefore, by using (S'1+S'2)/S'3 as a feature value and calculating a variation of the feature value, a cuff pressure when the feature value becomes a predetermined value may be estimated to be the systolic blood pressure. Note that S'2/S'3, which only uses two out of S'1, S'2, and S'3, may be also used as a feature value. Furthermore, a pulse wave may be divided into four or more.

In the present example embodiment, a relational expression f(X) is generated by means of the least-squares method, the relational expression may be generated by means of a different method as long as it enables estimation of the systolic blood pressure with high precision. Although, in the present example embodiment, a pulse wave is used, a differential pulse wave obtained by temporally differentiating a pulse wave may be used.

Second Example Embodiment

In the first example embodiment, an area ratio of areas before and after an extreme value of a pulse wave is used as a feature value, and utilizing symmetry of the pulse wave about the extreme value, a cuff pressure when the area ratio becomes approximately 1 is estimated to be the systolic blood pressure. It would be safe to say that the case where the area ratio becomes approximately 1 is a case where shapes of the pulse wave are approximately the same before and after the extreme value. Therefore, a feature value other than the area ratio may enable a relational expression to be calculated.

In the present example embodiment, instead of the area ratio, a slope ratio is used. For example, as illustrated in FIGS. 5(a) and 5(b), a ratio of an absolute value of a slope a1 of a straight line connecting the local minimum value immediately before a maximal value with the maximal value to an absolute value of a slope a2 of a straight line connecting the local minimum value immediately after the maximal value with the maximal value in a pulse waveform for each pulse may be used.

Figure 5:
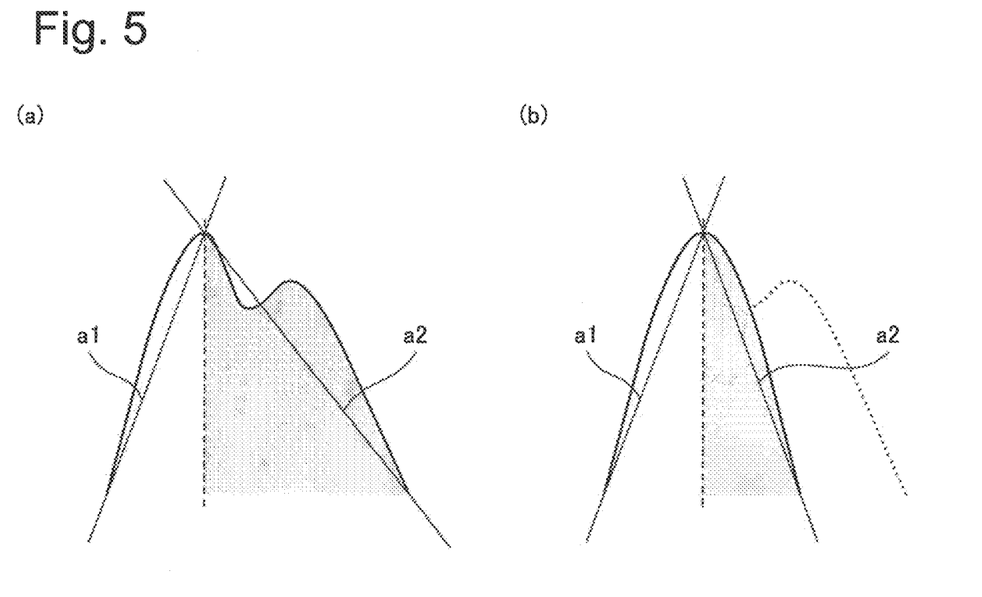
FIG. 5 is a diagram for explaining a second example embodiment according to the present invention.

Although the maximal value is used in FIGS. 5(a) and 5(b), a point of time shifted from the point of time for the maximal value may be used. For example, a slope ratio of two straight lines connecting a point shifted from the point of time for the maximal value with points having the local minimum values immediately before and after the point may be used. Alternatively, instead of the local minimum values, a point of time at which a pulse pressure of the pulse wave becomes 0 mmHg may be used, or a point of time at which the pulse pressure becomes m % of the wave height may be used.

Furthermore, although a pulse waveform is divided into two sections in the present example embodiment, the number of sections is not limited to two, and the waveform may be divided into a plurality of sections.

In the present example embodiment, it is just required that the pulse wave information calculating unit 13 include a function for calculating an absolute value of a slope of a pulse wave. Other configurations of the sphygmomanometer may be similar to those in the first example embodiment.

Third Example Embodiment

Other than the area ratio and the slope ratio, a time ratio, which is, for example, a ratio of a time period between a local minimum value and a maximal value in a pulse waveform for each pulse to a time period between the maximal value and the next local minimum value, may be used as the feature value. A cuff pressure when a ratio of these two time periods becomes approximately 1 is treated as the systolic blood pressure, similarly to the case where the area ratio is approximately 1.

Figure 6:
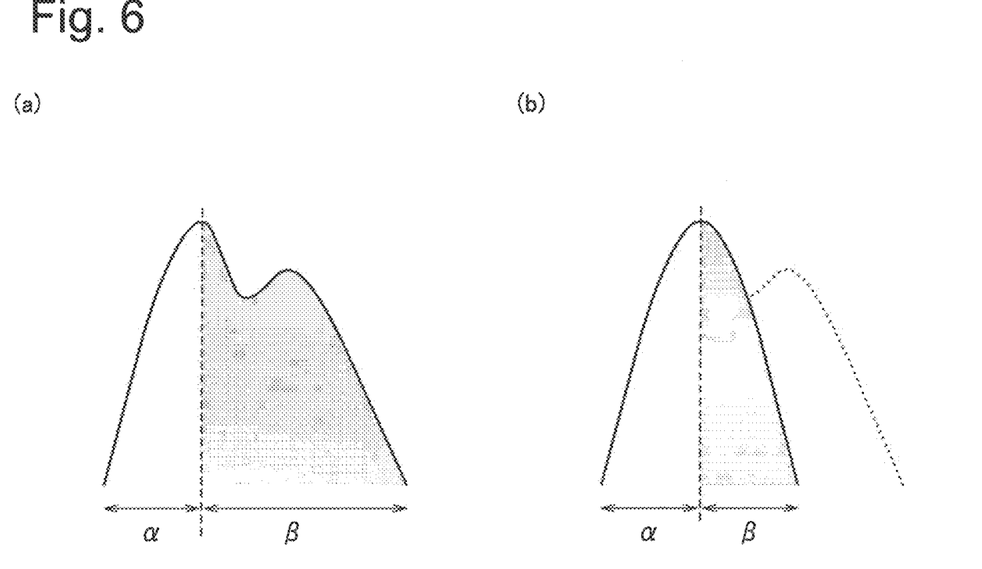
FIG. 6 is a diagram for explaining a third example embodiment according to the present invention.

In the present example embodiment, it is just required that the pulse wave information calculating unit 13 includes a function for calculating a time period $\alpha$ between a local minimum value and a maximal value in a pulse waveform for each pulse and a time period $\beta$ between the maximal value and the next local minimum value. As illustrated in FIGS. 6(a) and 6(b), since $\alpha/\beta<1$ corresponds to S1/S2<1 while $\alpha/\beta\approx4$ corresponds to S1/S2$\approx$1, a relational expression is generated by the blood pressure estimating unit 17 as in the first example embodiment, and a cuff pressure when $\alpha/\beta\approx4$ holds is estimated to be the systolic blood pressure.

Although the maximal value is used in FIGS. 6(a) and 6(b), a point of time shifted from the point of time for the maximal value may be used. When dividing the pulse wave at a point of time temporally earlier than the point of time for the maximal value, $\alpha/\beta$, which is estimated to be the systolic blood pressure, becomes less than 1. On the other hand, when dividing the pulse wave at a point of time temporally later than the point of time for the maximal value, $\alpha/\beta$, which is estimated to be the systolic blood pressure, becomes greater than 1.

Alternatively, a time period up to a point having a value approximately half of the wave height of a maximal value in a pulse waveform for each pulse may be defined as the feature value. In other words, a ratio of a time period between a point having a value approximately half of the wave height of the maximal value and the maximal value in the pulse waveform for a pulse before the maximal value to a time period between the maximal value and a point having a value approximately half of the wave height of the maximal value in the waveform after the maximal value may be used.

Furthermore, as it is understood from FIG. 4(a), in most pulse waves, the pulse pressure of a pulse wave for each pulse crosses 0 mmHg twice. Therefore, instead of the time period up to the point having a value approximately half of the wave height of the maximal value, a point of time at which the pulse pressure become zero may be used. Alternatively, a point of time at which the pulse pressure becomes m % of the wave height may be used. Furthermore, although a pulse waveform is divided into two sections in the present example embodiment, the number of sections is not limited to two, and the waveform may be divided into a plurality of sections.

Fourth Example Embodiment

Figure 7:
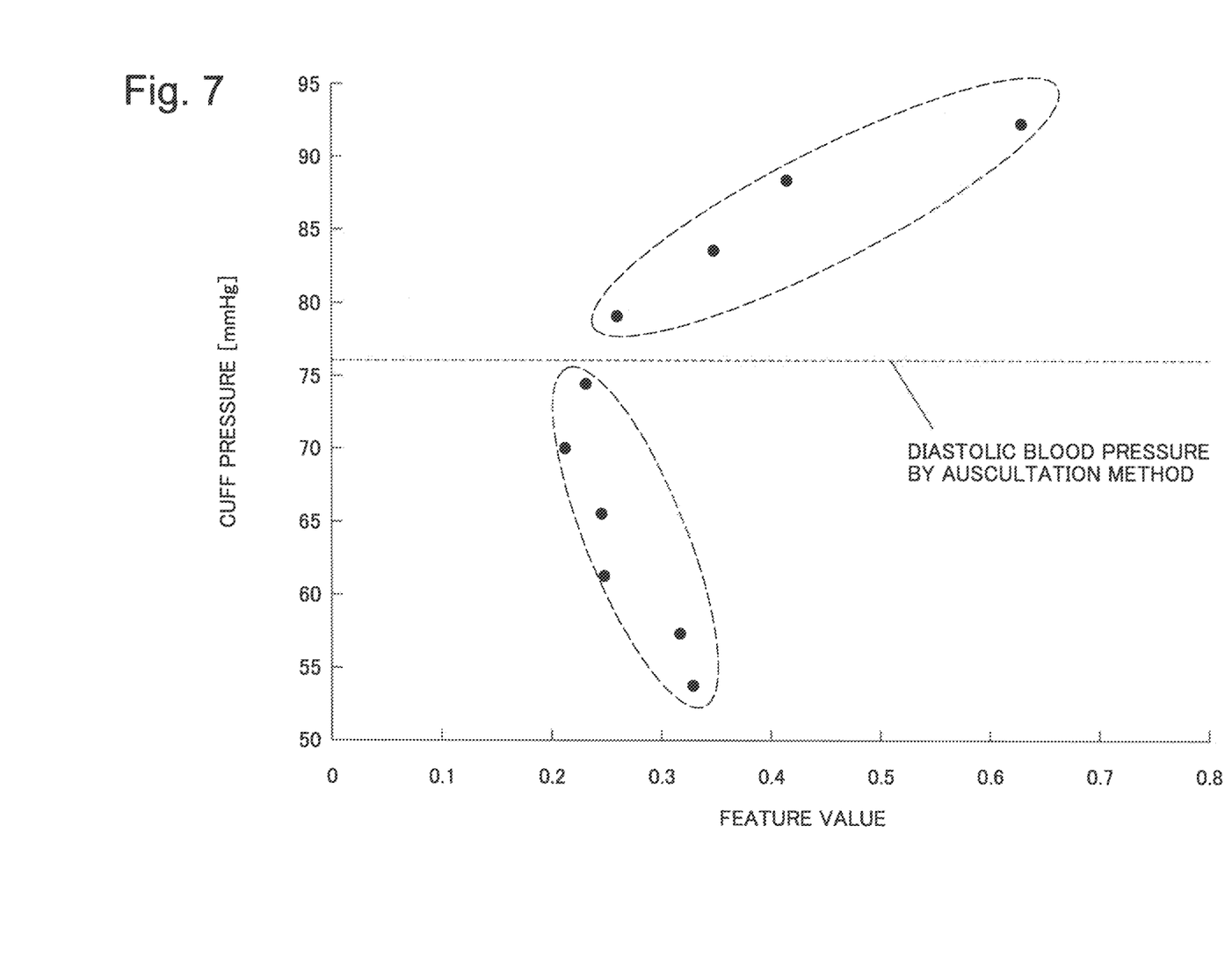
FIG. 7 is a diagram for explaining a fourth example embodiment according to the present invention.

Although, in the first example embodiment, it is described that an existing method such as the oscillometric method may be used for the diastolic blood pressure, it is possible to estimate the diastolic blood pressure by means of the technique of the present invention. FIG. 7 is a graph of the feature value and the cuff pressure in which the feature value is plotted on the horizontal axis and the cuff pressure is plotted on the vertical axis (the vertical axis and the horizontal axis are swapped with each other compared with FIG. 4). FIG. 7 is a graph for a step where the cuff is pressurized and the pulse waveform is yet to reach the maximum amplitude.

The diastolic blood pressure by means of the auscultation method is 76 mmHg as shown by the dashed line in FIG. 7. In FIG. 7, the plotted values above 76 mmHg have a trend diagonally left down while the plotted values below 76 mmHg have a trend diagonally left up; thus, it is found that the trend of the plotted values changes at 76 mmHg being the turning point. The point at which the two groups of plotted values enclosed by dashed lines having different trends meet and the diastolic blood pressure by means of the auscultation method are approximately coincident. Therefore, the point where trends of the two groups of plotted values change may be estimated to be the diastolic blood pressure. The diastolic blood pressure may be estimated using the pulse wave information calculating unit 13 and the blood pressure estimating unit 17.

Alternatively, by generating a relational expression with respect to each of the plotted values above the diastolic blood pressure and the plotted values below the diastolic blood pressure by means of the least-squares method, an intersection of the two relational expressions may be estimated to be the diastolic blood pressure. The method of generating the relational expression may be the same as in the first to third example embodiment. The relational expression may be generated by means of a method other than the least-squares method.

Fifth Example Embodiment

Figure 8:
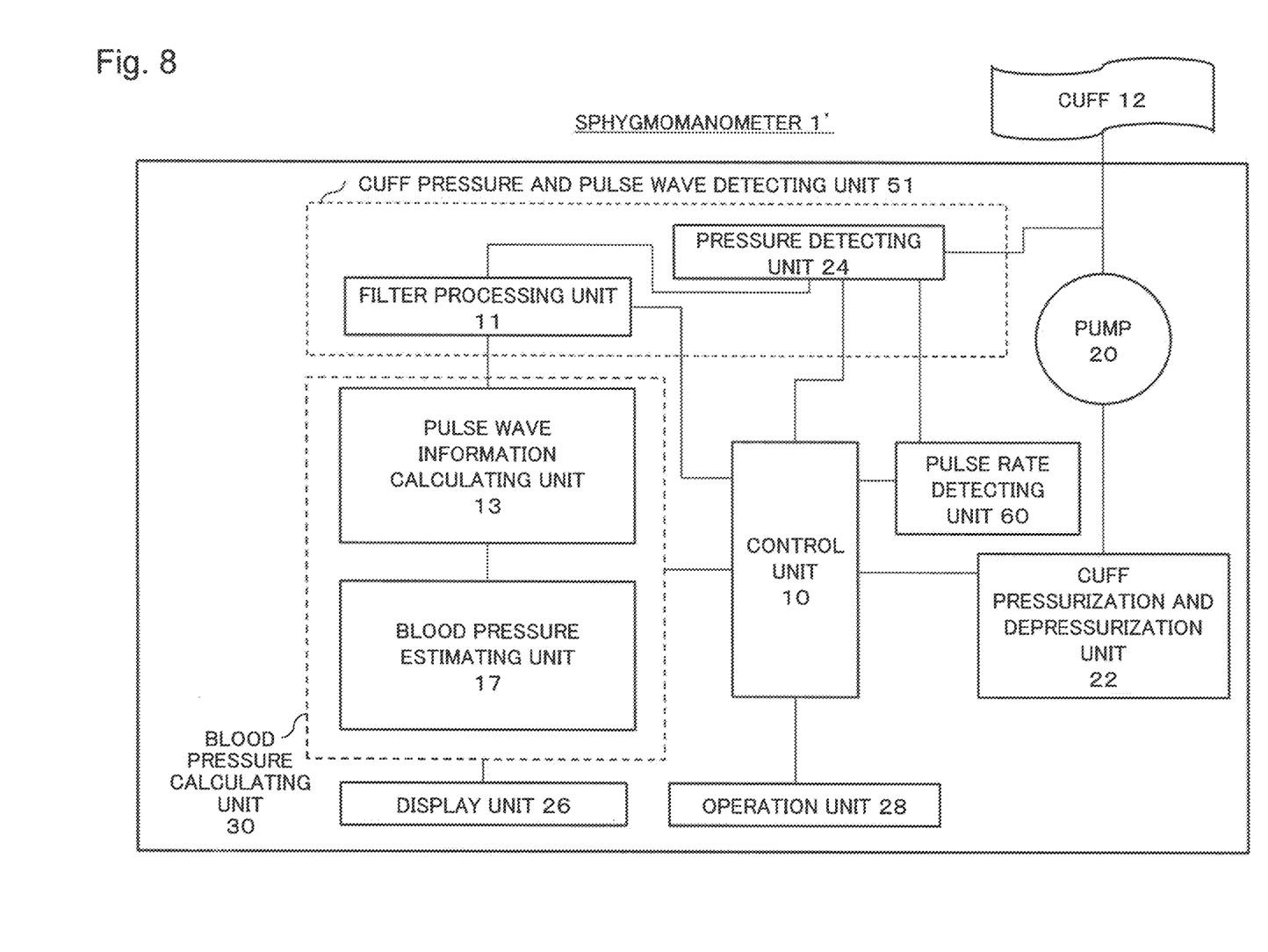
FIG. 8 is a block diagram illustrating a configuration of a sphygmomanometer of a fifth example embodiment according to the present invention.

FIG. 8 is a block diagram for explaining a sphygmomanometer 1' of a fifth example embodiment according to the present invention. The sphygmomanometer 1' of the present example embodiment differs from the sphygmomanometer of the first example embodiment in that it includes a pulse rate detecting unit 60. When a pulse rate of a person to be measured is low, the point for stopping pressurization (for example, the N-th pulse after a maximum amplitude appears) may exceed the systolic blood pressure. In this case, a pulse rate should be measured while pressurizing the cuff by adjusting a pressurization rate according to a magnitude of the pulse rate. When the pulse rate is low, the point for stopping pressurization may be set before the systolic blood pressure by decreasing the pressurization rate. On the other hand, when the pulse rate is high, the measurement time may be shortened by increasing the pressurization rate.

The pulse rate detecting unit 60 acquires a pressure of a pulse wave from the pressure detecting unit 24 and detects a pulse rate. The data of the detected pulse rate is transmitted to the control unit 10.

Sixth Example Embodiment

Figure 9:
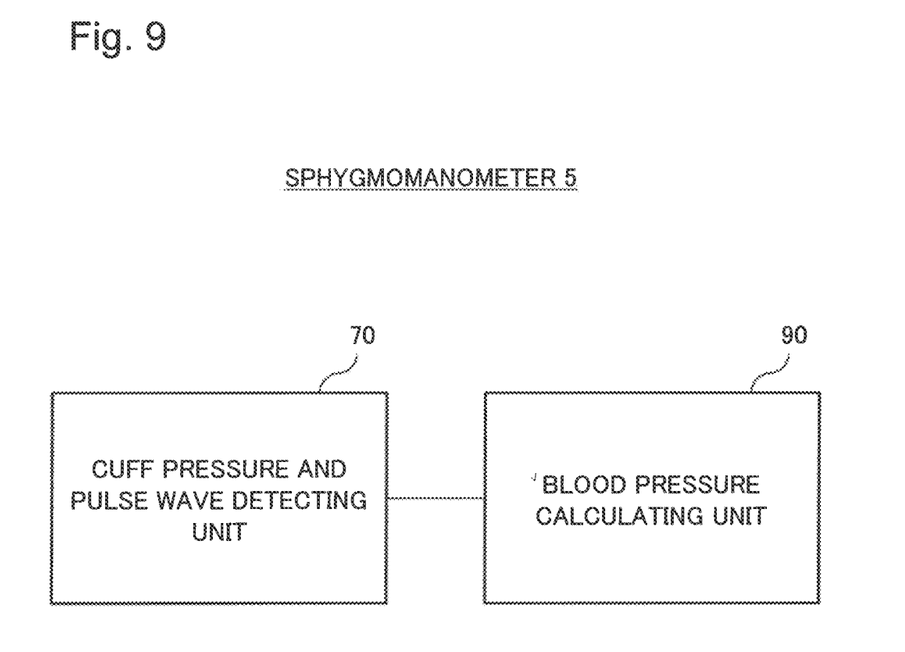
FIG. 9 is a block diagram for explaining a sixth example embodiment according to the present invention.

FIG. 9 is a block diagram illustrating a sphygmomanometer 5 of a sixth example embodiment. The sphygmomanometer 5 includes a cuff pressure and pulse wave detecting unit 70 and a blood pressure calculating unit 90. The cuff pressure and pulse wave detecting unit 70 detects a cuff pressure and a pulse wave. The blood pressure calculating unit 90 divides the pulse wave detected by the cuff pressure and pulse wave detecting unit 70 in a particular period into a plurality of sections, and calculates an estimated value of a systolic blood pressure from fluctuation in symmetry of pulse waveforms of the plurality of sections caused by variation of the cuff pressure. In this way, a blood pressure may be measured without compressing the cuff to the systolic blood pressure and in a short period of time.

Other Example Embodiments

Although the area, the slope and the time period are individually used as the feature value in the aforementioned first to sixth example embodiments, they may be used in conjunction with each other as needed. For example, the mean value of any two or all of the three may be used as the estimated value.

Note that the sphygmomanometer according to the present invention may be applicable to measurement of blood pressure of not only humans but also animals such as dogs or cats.

Furthermore, in the aforementioned first to sixth example embodiments, the sphygmomanometer is realized as a dedicated device; however, it may be realized using a computer (information processing apparatus). In this case, the computer may read out a software program stored in a memory to a CPU (Central Processing Unit) and execute the read software program on the CPU.

The present invention has been described above by exemplifying the aforementioned example embodiments as exemplary examples. However, the present invention is not limited to the aforementioned example embodiments. In other words, various aspects that would be understood by those skilled in the art are applicable to the present invention within the scope of the present invention.

Some or all of the aforementioned example embodiments may be described as in the following supplementary notes, but are not limited to the following.

(Supplementary note 1)

A sphygmomanometer, characterized in that the sphygmomanometer includes a cuff pressure and pulse wave detecting unit configured to detect a cuff pressure and a pulse wave and a blood pressure calculating unit configured to divide the pulse wave detected by the cuff pressure and pulse wave detecting unit in a particular period into a plurality of sections and calculate an estimated value of a systolic blood pressure from fluctuation in symmetry of pulse waveforms of the plurality of sections caused by variation of the cuff pressure detected by the cuff pressure and pulse wave detecting unit.

(Supplementary note 2)

The sphygmomanometer according to the supplementary note 1, characterized in that pressurization stops at a pressure lower than the systolic blood pressure.

(Supplementary note 3)

The sphygmomanometer according to the supplementary note 1 or 2, characterized in that the blood pressure calculating unit divides a pulse wave in a particular period into a plurality of sections, and calculates an estimated value of a systolic blood pressure from a variation between area ratios of the plurality of sections caused by variation of the cuff pressure.

(Supplementary note 4)

The sphygmomanometer according to any one of the supplementary notes 1 to 3, characterized in that the blood pressure calculating unit divides a pulse wave in a particular period into a plurality of sections, and calculates an estimated value of a systolic blood pressure from a variation between slope ratios of the plurality of sections caused by variation of the cuff pressure.

(Supplementary note 5)

The sphygmomanometer according to any one of the supplementary notes 1 to 4, characterized in that the blood pressure calculating unit divides a pulse wave in a particular period into a plurality of sections, and calculates an estimated value of a systolic blood pressure from a variation between time ratios of the plurality of sections caused by variation of the cuff pressure.

(Supplementary note 6)

The sphygmomanometer according to any one of the supplementary notes 3 to 5, wherein the blood pressure calculating unit divides the pulse wave in the particular period into two sections, and estimates a cuff pressure at which at least one of the area ratio, the slope ratio, and the time ratios becomes approximately 1 to be the systolic blood pressure.

(Supplementary note 7)

The sphygmomanometer according to any one of the supplementary notes 1 to 6, characterized in that the pulse wave is divided into a plurality of sections for each pulse.

(Supplementary note 8)

The sphygmomanometer according to any one of the supplementary notes 1 to 7, characterized in that the blood pressure calculating unit divides the pulse wave in the particular period into a plurality of sections, and treats a cuff pressure at which a trend of fluctuation in symmetry of the pulse waveforms of the plurality of sections caused by variation of the cuff pressure changes as a diastolic blood pressure.

(Supplementary note 9)

The sphygmomanometer according to any one of the supplementary notes 1 to 8, wherein the particular period is a predetermined period of time before the cuff pressure reaches a systolic blood pressure.

(Supplementary note 10)

The sphygmomanometer according to any one of the supplementary notes 1 to 9, characterized in that the sphygmomanometer further includes a pulse rate detecting unit, detects a pulse rate in a process of pressurizing a cuff, and adjusts a pressurization rate according to the pulse rate.

(Supplementary note 11)

The sphygmomanometer according to any one of the supplementary notes 1 to 10, characterized in that the sphygmomanometer calculates a diastolic blood pressure in the process of pressurizing the cuff, stops pressurization at a point of time at which the diastolic blood pressure is obtained, and immediately performs depressurization.

(Supplementary note 12)

The sphygmomanometer according to any one of the supplementary notes 1 to 11, characterized in that a site for attaching the cuff contains at least one of a brachial artery, a carotid artery, a superficial temporal artery, a facial artery, a radial artery, a femoral artery, a popliteal artery, a posterior tibial artery, and a *dorsalis* pedis artery.

(Supplementary note 13)

A blood pressure measurement method, characterized in that a cuff pressure and a pulse wave are detected, the detected pulse wave is divided in a particular period into a plurality of sections, and an estimated value of a systolic blood pressure is calculated from fluctuation in symmetry of pulse waveforms of the plurality of sections caused by variation of the detected cuff pressure.

(Supplementary note 14)

A blood pressure measurement program, characterized in that the program causes a computer to execute a cuff pressure and pulse wave detecting process for detecting a cuff pressure and a pulse wave as well as a process for dividing the pulse wave detected by the cuff pressure and pulse wave detecting unit in a particular period into a plurality of sections and calculating an estimated value of a systolic blood pressure from fluctuation in symmetry of pulse waveforms of the plurality of sections caused by variation of the cuff pressure detected by the cuff pressure and pulse wave detecting unit."

This application claims priority to Japanese Patent Application No. 2016-065726 filed on Mar. 29, 2016, the entire disclosure of which is incorporated herein.

REFERENCE SIGNS LIST 1, 1', 5 sphygmomanometer
10 control unit
11 filter processing unit
12 cuff
13 pulse wave information calculating unit
17 blood pressure estimating unit
20 pump
22 cuff pressurization and depressurization unit
24 pressure detecting unit
26 display unit
28 operation unit
30 blood pressure calculating unit
51 cuff pressure and pulse wave detecting unit
60 pulse rate detecting unit
70 cuff pressure and pulse wave detecting unit
90 blood pressure calculating unit

What is claimed is:

1. A sphygmomanometer comprising:
a cuff;
a cuff pressure and pulse wave detecting unit configured to detect a cuff pressure at a plurality of pulse waves while the cuff is being pressurized; and
a blood pressure calculating unit configured to
for each pulse wave:
identify a first minimum time at which the pulse wave is at a minimum value, identify a second minimum time, later than the first minimum time, at which the pulse wave is next at the minimum value, and identify a maximum time, between the first minimum time and the second minimum time, at which the pulse wave is at a maximum value;
calculate a first area of a first waveform between the first minimum time and the maximum time and a second area of a second waveform between the maximum time and the second minimum time, and calculate a first ratio between the first area and the second area;
calculate a first slope of a first line between the first minimum time and the maximum time and a second slope of a second line between the maximum time and the second minimum time, and calculate a second ratio between an absolute value of the first slope and an absolute value of the second slope;
calculate a first time length between the first minimum time and the maximum and a second time length between the maximum time and the second minimum time, and calculate a third ratio between the first time length and the second time length;
identify the pulse wave at which the first ratio is first ratio is approximately one, as a first pulse wave, identify the pulse wave at which the second ratio is approximately one, as a second pulse wave, and identify the pulse wave at which the third ratio is approximately one, as a third pulse wave; and
estimate a systolic blood pressure from the cuff pressure at the first pulse wave, the cuff pressure at the second pulse wave, and the cuff pressure at the third pulse wave.

2. The sphygmomanometer according to claim 1, wherein the cuff pressure at which the first, second or third ratio becomes approximately one is calculated from a relational expression obtained from a relationship between the cuff pressure before reaching the systolic blood pressure and the first, second or third ratio and is estimated as systolic blood pressure.

3. The sphygmomanometer according to claim 1, further comprising:
a pulse rate detecting unit to detect a pulse rate while the cuff is being pressurized and to adjust a pressurization rate at which the cuff is being pressurized according to the pulse rate.

4. The sphygmomanometer according to claim 1, wherein the blood pressure calculating unit is further to calculate a diastolic blood pressure while the cuff is being pressurized, stop pressurization of the time at a point of time at which the diastolic blood pressure is calculated, and immediately perform depressurization.

5. The sphygmomanometer according to claim 1, wherein a site for attaching the cuff contains at least one of a brachial artery, a carotid artery, a superficial temporal artery, a facial artery, a radial artery, a femoral artery, a popliteal artery, a posterior tibial artery, and a *dorsalis* pedis artery.

6. A blood pressure measurement method comprising:
   detecting a cuff pressure at a plurality of pulse waves while a cuff is being pressurized;
   for each pulse wave:
      identifying a first minimum time at which the pulse wave is at a minimum value, identifying a second minimum time, later than the first minimum time, at which the pulse wave is next at the minimum value, and identifying a maximum time, between the first minimum time and the second minimum time, at which the pulse wave is at a maximum value;
      calculating a first area of a first waveform between the first minimum time and the maximum time and a second area of a second waveform between the maximum time and the second minimum time, and calculating a first ratio between the first area and the second area;
      calculating a first slope of a first line between the first minimum time and the maximum time and a second slope of a second line between the maximum time and the second minimum time, and calculating a second ratio between an absolute value of the first slope and an absolute value of the second slope;
      calculating a first time length between the first minimum time and the maximum and a second time length between the maximum time and the second minimum time, and calculating a third ratio between the first time length and the second time length;
   identifying the pulse wave at which the first ratio is first ratio is approximately one, as a first pulse wave, identifying the pulse wave at which the second ratio is approximately one, as a second pulse wave, and identifying the pulse wave at which the third ratio is approximately one, as a third pulse wave; and
   estimating a systolic blood pressure from the cuff pressure at the first pulse wave, the cuff pressure at the second pulse wave, and the cuff pressure at the third pulse wave.

7. A non-transitory computer-readable recording medium that records a blood pressure measurement program, wherein the program causes a computer to execute a cuff pressure and pulse wave detecting process comprising:
   detecting a cuff pressure at a plurality of pulse waves while a cuff is being pressurized;
   for each pulse wave:
      identifying a first minimum time at which the pulse wave is at a minimum value, identifying a second minimum time, later than the first minimum time, at which the pulse wave is next at the minimum value, and identifying a maximum time, between the first minimum time and the second minimum time, at which the pulse wave is at a maximum value;
      calculating a first area of a first waveform between the first minimum time and the maximum time and a second area of a second waveform between the maximum time and the second minimum time, and calculating a first ratio between the first area and the second area;
      calculating a first slope of a first line between the first minimum time and the maximum time and a second slope of a second line between the maximum time and the second minimum time, and calculating a second ratio between an absolute value of the first slope and an absolute value of the second slope;
      calculating a first time length between the first minimum time and the maximum and a second time length between the maximum time and the second minimum time, and calculating a third ratio between the first time length and the second time length;
   identifying the pulse wave at which the first ratio is first ratio is approximately one, as a first pulse wave, identifying the pulse wave at which the second ratio is approximately one, as a second pulse wave, and identifying the pulse wave at which the third ratio is approximately one, as a third pulse wave; and
   estimating a systolic blood pressure from the cuff pressure at the first pulse wave, the cuff pressure at the second pulse wave, and the cuff pressure at the third pulse wave.

* * * * *